United States Patent [19]

Beard

[11] 4,328,907
[45] May 11, 1982

[54] DISPENSER FOR INDIVIDUAL MOISTENED PAPER TISSUES FROM A LENGTH THEREFOR PERFORATED AT INTERVALS

[75] Inventor: Michael J. Beard, Blackwater, England

[73] Assignee: Medi-Pack Limited, Surbiton, England

[21] Appl. No.: 101,082

[22] Filed: Dec. 7, 1979

[30] Foreign Application Priority Data

Jan. 2, 1979 [GB] United Kingdom ................. 7900030

[51] Int. Cl.³ .............................................. B65H 1/00
[52] U.S. Cl. ................................................... 221/63
[58] Field of Search ...................... 221/63, 33, 40, 50; 206/410, 205; 222/498, 562, 543, 545

[56] References Cited

U.S. PATENT DOCUMENTS

| 3,208,650 | 9/1965 | Ham | 222/543 |
| 3,322,308 | 5/1967 | Foster | 222/498 X |
| 3,843,017 | 10/1974 | Harrison | 221/63 |
| 4,017,002 | 4/1977 | Doyle et al. | 221/63 |
| 4,138,034 | 2/1979 | McCarthy | 221/63 |
| 4,219,129 | 8/1980 | Sedgwick | 221/63 |

FOREIGN PATENT DOCUMENTS 2405793 9/1974 Fed. Rep. of Germany ........ 221/63

*Primary Examiner*—Stanley H. Tollberg
*Attorney, Agent, or Firm*—Robert F. O'Connell

[57] ABSTRACT

A dispenser from which may be pulled individual, moist, non-woven fabric wipes, comprising: a container body; a linked succession of the moist, non-woven fabric wipes located generally within the container body; a container lid removably attached over an open upper end of the body; a wall surrounding a central portion of the lid which the central portion includes an orifice to receive the end wipe in the succession of wipes; the orifice having both a fixed length and a fixed breadth and approaching at its edges the surrounding wall; and temporary closure and sealing members locatable at an upper edge of the surrounding wall to close the orifice between dispensations.

2 Claims, 10 Drawing Figures

U.S. Patent May 11, 1982 4,328,907
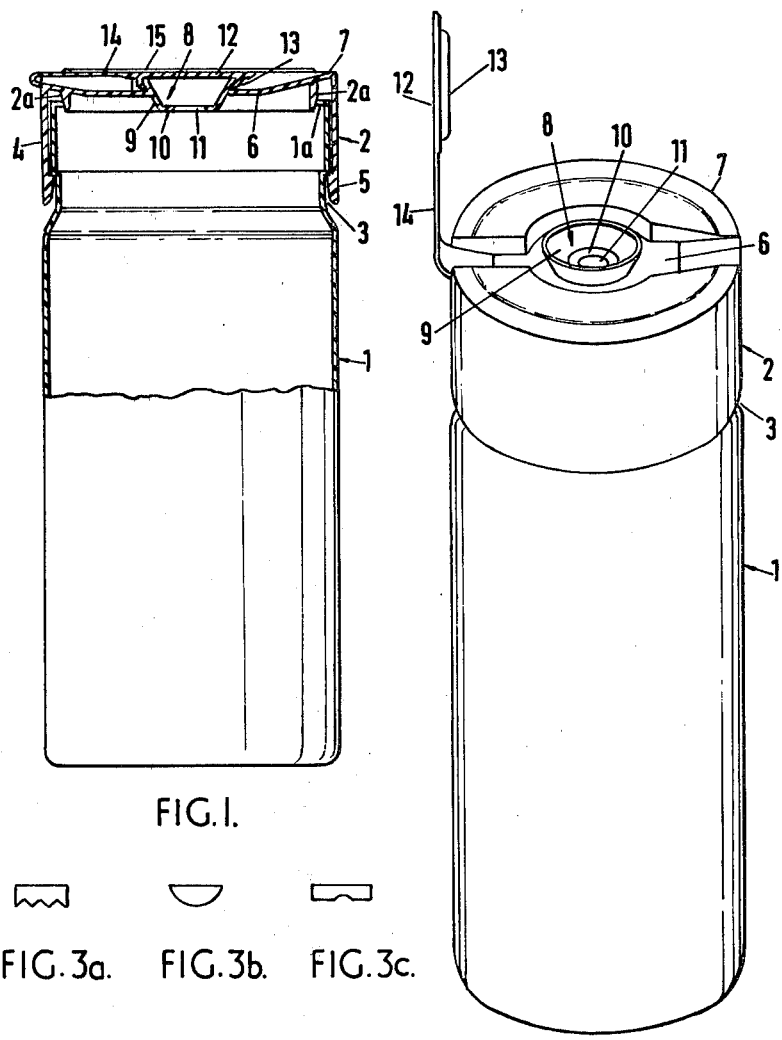

DISPENSER FOR INDIVIDUAL MOISTENED PAPER TISSUES FROM A LENGTH THEREFOR PERFORATED AT INTERVALS

This invention relates to a dispenser for a linked succession of fibrous pads or wipes.

It is well known to provide sealed foil or like impervious sachets each one containing one or two moistened and/or medicated impregnated fabric or paper sheets. Typically, these include a non-woven fabric such as a paper, impregnated with an alcohol-based perfume and/or medicament. Such wipes are used as face wipes or medical wipes e.g. prior to injections.

It is also known to provide a linked succession of such wipes to save the opening of individual sachets, especially for repeated use in a medical context such as surgical wipes. The wipes in the linked succession must resist drying out in storage and must also resist drying out over the period of use of the whole chain after the container is opened.

One typical prior proposal has been to store the linked succession of moist non-woven fabric wipes, with tear lines between the individual wipes defined by spaced perforations, within a closed cylindrical container of synthetic polymeric material. The wipes are typically stored within the container as a loose roll. For use, the lid of the container is removed, and the end wipe (usually from the inside of the roll) is extracted and put into a slit in this lid, which is then replaced. Successive wipes are then thereafter pulled through the slit, each by the action of the preceding wipe before it tears off. The torn end is protected with a tight-fitting cover over the slit.

Hitherto, it has always been felt necessary to provide the orifice in the lid as a slit, either by a simple straight slit, or a cruciform slit, or some more complicated arrangement of slits defining teeth or the like. The slit orifice has been believed to be a source of moisture loss over the period of use, and therefore it has been felt that it must tend to close itself and define as a small an open area as possible between successive dispensing.

We have now discovered however that it is not necessary to use a slit and that improved results are surprisingly obtained by the use of a non-linear orifice of fixed dimension in the lid.

The invention accordingly consists in a container for a linked succession of moist non-woven-fabric wipes in which the lid of the container exhibits a non-linear orifice of fixed dimension through which the wipes can be pulled, prior to being individually torn off, temporary closure and sealing means being provided over the said orifice between such dispensations.

It will be described in more detail below, the hole can be of any shape which is of fixed dimension i.e. which does not vary in use. It can be symmetrical or quasi-symmetrical about its centre, or can be symmetrical about a plane of symmetry, or can be non-symmetrical. Thus, it can be for example circular, triangular, semicircular, or rectangular. If rectangular the long side can optionally be provided with rigid projections, but it is important to appreciate that such projections are not distorted by passage of the non-woven fabric material past them.

Preferably, the orifice is circular and from 3–10 mm diameter, more preferably from 5–8 mm diameter; if non-circular, it will most preferably possess equivalent areas to these.

Usually, the orifice will have a surrounding wall over the rim of which a temporary sealing cap fits during the periods between dispensation, thereby constituting the closure and sealing means. Preferably, the orifice is spaced from the sealing cap so that a closed volume is located within these surrounding walls and inside the cap, to accommodate the torn end of the next wipe. In one preferred form of the invention these surrounding walls taper inwardly in a frusto-conical manner, the orifice being provided in the narrower base of this section and the temporary closure fitting over the broader upper rim. The closure can be integral with an attaching strap itself flexible and integrally connected to part of the lid.

It is further advantageous if the lid indicates a preferred direction of removal for the wipes, for reasons which are discussed in more detail below, and if moreover finger-pressure areas are defined thereon.

The lid can have (i) a peripheral depending skirt terminating in a thickened rim to fit into a corresponding circumferential recess in the body of a cylindrical or like synthetic polymeric vessel which contains the roll of linked wipes, and (ii) an integral flexible tapering ring extending from the underside of, and coaxial with, the lid, to engage with the inner edge of an internally directed flexible integral peripheral flange at the top of the vessel. Such a roll is normally of a loose configuration and may indeed be distorted from its normal cylindrical shape.

If the container as provided for storage prior to a period of use there is conventionally (a) a seal around the join between the lid and the vessel and (b) a paper or polymer film seal over the face of the lid.

The invention will be further described with reference to the accompanying drawings in which:

FIG. 1 is a partial cross-section through a container and associated lid according to the invention, FIG. 2 is a perspective view of the top of such a container with the temporary closure raised, FIGS. 3a, 3b and 3c show alternative shapes of orifice which can be provided in such a lid, and FIGS. 4a to 4e show diagrammatically the reasons believed to lead to the improvement obtained by use of the present invention, insofar as these are shown to the applicants.

In FIG. 1 a vessel 1 is provided with a lid 2 around its open upper end.

Vessel 1 has, towards it open upper end, a peripheral recess 3. Lid 2 has a surrounding downwardly extending skirt 4 ending in thickened rim 5 which fits in this recess and hold the lid securely in place. In storage, prior to periods of use, this basic attachment is completed by a strip of pressure-sensitive adhesive tape (not shown) extending around the join at recess 3 and contacting both the vessel and its lid.

The upper surface of the lid is generally planar to provide a finger-pressure surface, but has a central zone 6 (see FIG. 2) somewhat below this level 7 of the top of the lid. In this depressed central zone 6 there is provided a frusto-conical structure 8, with surrounding tapering walls 9 and base 10 with central orifice 11. At the upper rim of this frusto-conical structure 8 there is provided a sealing closure 12 (the top surface of which is at a level with the top surface of the lid) possessing on its underside a circular projection 13 to fit over the rim of the frusto-conical surrounding wall 9. This closure 12 is connected by integral flap 14 to the main body of the lid, and the whole of the flat top of the lid is provided with a circular leaf 15 of paper or polymer, coated on its underside with an adhesive, for storage purposes prior to use.

FIG. 2 shows the integers of FIG. 1 but in perspective with the adhesive tape and paper leaf seals removed, the closure 12 lifted, and the container ready for use.

The exact nature of the interconnection between the lid 2 and vessel 1 is shown by the integers 3 and 5 on the one hand and 1a and 2a on the other.

As already stated, a circumferential recess 3 in the vessel 1 accommodates a thickened rim 5 of the lid to give a positive mechanical closure resistant to casual or accidental displacement. Also, because of the flexibility of the materials there is a sealing effect around this junction.

At the top of the vessel there is an internally directed flexible integral peripheral flange 1a engaging at its inner edge with a tapering surface of an integral flexible ring 2a extending from the underside of, and coaxial with lid 2.

Thus, when the two parts, lid and vessel, are assembled firstly the thickened rim 5 pushes down around the uppermost part of vessel 1, possibly deforming inwards slightly this uppermost part; and thereafter the rim 5 snaps into recess 3 and the flange 1a is forced upwards against the tapering wall 2a to give a good seal against loss of moisture.

It will be apparent from FIG. 2 that the orifice 11 is circular in plan view. However, this is not essential, and other shapes can be chosen. FIGS. 3a, 3b, and 3c show other typical shapes.

The container as shown, which is distinguished over the prior art primarily by the provision of an orifice of fixed shape rather than by provision of a slit with flexible edges appears to give improved results for the following reasons, although it is not applicant's intention to be found by such reasons over and above the requirements of the claims appended hereto.

FIG. 4a shows a prior art cruciform slit which is uniformly opened, as would be the case if a uniform deformable cylindrical body of material was being pulled at 90° through the centre. In FIG. 4a the material is shown deformed at 17, and the cruciform slit has taken up the symmetrical star-shaped configuration 18. If on the other hand, the material is pulled out somewhat to one side the actual opening of the slit is rather as shown in FIG. 4b, which is completely different and gives a different type and strength of restraint. This clearly gives a different shape to the material 19 and a different outline to the slits 20.

If the cylindrical body of material (i.e. the emerging wipe) is pulled in a further slightly different direction a shape somewhat as shown as FIG. 4c was achieved, with the deformable material again adopting a different shape 21 and the slit being deformed as shown at 22. Thus, even given a notionally uniform cylinder of deformable material emerging from the orifice, the prior art depending upon the direction of pull exert considerably different restraining forces upon the material. This is exacerbated by the circumstances that the emerging wipe is (a) not strictly cylindrical and (b) varies in cross-section both along the distance represented by one individual wipe and in any case from the beginning of the succession of wipes to the end of the succession. Sometimes, the wipe emerges as a more or less uniform cylinder, but at other times it comes out as a pleated or crumpled body and sometimes as a body with slightly different amounts of moisture along its emerging length, especially if the container has been stood unused a few hours so that the high amount of moisture present can sink to the bottom.

The net effect of all this is that instead of the successive wipes tearing off at a more or less fixed distance from the orifice, (when the pull upon them overcomes the resistance at the perforations), they tear at varying distances from the orifices. Thus, sometimes there is too short a length of material to grip easily protruding from the teeth and at other times almost a full wipe left protruding. In the former case the lid must be taken off and the wipe pushed through from beneath until a sufficient length is projecting to be gripped properly. In the latter case, there is a danger that the protruding wipe will dry out and when pulled will break off at the teeth since this marks the juncture of the relatively dry and relatively wet paper. In either case, therefore, the lid must be removed and the situation remedied.

We have found that if a hole of fixed size is used it provides substantially fixed (or at least much more uniform) resistance to passage of the wipes, and that this dominates the variability otherwise given by irregularities in folding moisture content, etc of successive sheets.

If a small circular orifice is used, for example all parts of the periphery contact the paper in a uniform fashion as shown in FIG. 4d, where the bundle periphery 23 is the orifice periphery. This contacting of all of the periphery with the roll of material is greatly preferred. The exact dimensioning of the hole is a matter of experiment with the paper and impregnant in question, but we have generally found that a circular hole from 3 to 10 mm diameter is suitable for a range of moist wipe material from 25 to 80 gm/m$^2$ in weight and that a preferred range of from 5 to 8 mm will be suitable for a weight of 35–55 gm/m$^2$.

If larger circular orifices are used, they present configuration 24 to the paper and utilise for example, about half the periphery 25 in every case (as shown in FIG. 4e) in whichever direction the wipe is pulled in. While there is some consistency in this, a smaller orifice is more reliable.

Similarly, if a rectangular orifice is used, it can be seen that there are least two directions of pull which could conceivably differ in type. While therefore the resistance given by the whole of one longer wall to removal of the paper (i.e. if the paper is all pulled over this longer) is approximately equivalent to the resistance given by half of each of the long walls if the paper is pulled out sideways (i.e. over the narrow end), it is again preferred if the size is such as to contact the enlarging paper around the whole periphery. For this, and for other noncircular shapes, an area of orifice substantially equal to this discussed above for circular orifices is preferred.

Where the orifice is not symmetrical about its centre, it is preferred to have an indicated direction of pull, and the depressed area in the centre of the lid as shown in FIGS. 1 and 2 usefully defines such a direction. FIGS. 3a, 3b, and 3c are therefore to be understood as preferably having their long axes transverse to the general direction of the depressed area.

It will be apparent from FIGS. 3a and 3c in particular that fixed projections can be provided upon the wall of the orifice. This is not to be confused with the provision of flexible teeth defined between the slits of the prior art; such fixed projections are effectively to some extent a way of modifying the length of wall in contact with the sheet and to some extent a way of increasing the drag on the sheet by virtue of their shape. It is important to bear in mind however, that their restraining action is still essentially uniform and not fluctuating as is that of the teeth defined by the slits of the prior art.

In practice the use of an orifice of fixed size as described above does not unduly promote the loss of water vapour. Such an orifice is always generally closed by the next emerging wipe and is over reasonable period of non-use closed over by cover 13, whose sealing action is not destroyed by having to accommodate occasional unduly projecting lengths of wipes. Indeed, over a normal expected period of use, we believe that there is more moisture loss from the container as a result of periodic removals of the lid to re-insert the next wipe than there is with the structure according to the invention which, although having a larger orifice, provides uniformly emerging wipes and allows the lid 2 to be retained on the container for statistically significant longer periods.

I claim:

1. A dispenser from which may be pulled individual, moist, non-woven fabric wipes comprising a container body, a linked succession of said moist, non-woven fabric wipes located generally within said container body, a container lid removably attached over an open upper end of said body, a wall surrounding the central portion of said lid, which said central portion includes an orifice to receive the end wipe in said succession of wipes, said orifice having both a fixed length and a fixed breadth and approaching at its edges a surrounding wall and a lid located at the upper edge of said surrounding wall to close said orifice between dispensations, the upper surface of said lid having two areas, one to each side of said orifice for lid-retaining finger pressure when a wipe protruding from said orifice is pulled and spaced apart to define a marking indicating a preferred direction of pull.

2. A dispenser according to claim 1 in which the wall is frusto-conical with its smaller end surrounding the circular orifice.

* * * * *